United States Patent
Song et al.

(10) Patent No.: US 7,632,653 B2
(45) Date of Patent: *Dec. 15, 2009

(54) MEMBRANE-BASED ASSAY DEVICES THAT UTILIZE TIME-RESOLVED FLUORESCENCE

(75) Inventors: Xuedong Song, Roswell, GA (US); Rosann Kaylor, Cumming, GA (US); Michael Knotts, Roswell, GA (US); Ning Wei, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 534 days.

This patent is subject to a terminal disclaimer.

(21) Appl. No.: 10/286,342

(22) Filed: Nov. 1, 2002

(65) Prior Publication Data

US 2004/0043502 A1 Mar. 4, 2004

Related U.S. Application Data

(63) Continuation-in-part of application No. 10/228,836, filed on Aug. 27, 2002, now Pat. No. 7,285,424.

(51) Int. Cl.
*G01N 33/533* (2006.01)
(52) U.S. Cl. .................... 435/7.92; 435/3; 435/7.93; 435/7.94; 422/56; 422/82.07; 422/82.08; 436/800
(58) Field of Classification Search ............. 422/56, 422/82.07, 82.08; 436/800; 435/3, 7.92, 435/7.93, 7.94
See application file for complete search history.

(56) References Cited

U.S. PATENT DOCUMENTS 164,659 A 5/1875 Reckhow et al.
3,604,927 A 9/1971 Hirshfeld (Continued)

FOREIGN PATENT DOCUMENTS

EP 0073593 A1 3/1983

(Continued)

OTHER PUBLICATIONS

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

(Continued)

*Primary Examiner*—Bao-Thuy L Nguyen
(74) *Attorney, Agent, or Firm*—Dority & Manning, P.A.

(57) ABSTRACT

A membrane-based assay device for detecting the presence or quantity of an analyte residing in a test sample is provided. The device utilizes time-resolved fluorescence to detect the signals generated by excited fluorescent labels. Because the labels can have relatively long emission lifetime, short-lived background interference can be practically eliminated through delayed fluorescence detection. In addition, the resulting fluorescent reader can have a simple and inexpensive design. For instance, in one embodiment, the reader can utilize a silicon photodiode and a pulsed light-emitting diode (LED) to accurately excite labels and detect fluorescence on a membrane-based assay device without requiring the use of expensive components, such as monochromators or narrow emission band width optical filters.

28 Claims, 6 Drawing Sheets

U.S. PATENT DOCUMENTS

| | | |
|---|---|---|
| 3,835,247 A | 9/1974 | Soames |
| 4,006,360 A | 2/1977 | Mueller |
| 4,094,647 A | 6/1978 | Deutsch et al. |
| RE30,267 E | 5/1980 | Bruschi |
| 4,210,723 A | 7/1980 | Dorman et al. |
| 4,259,574 A | 3/1981 | Carr et al. |
| 4,312,228 A | 1/1982 | Wohltjen |
| 4,336,459 A | 6/1982 | Fay |
| 4,341,957 A | 7/1982 | Wieder |
| 4,361,537 A | 11/1982 | Deutsch et al. |
| 4,363,874 A | 12/1982 | Greenquist |
| 4,374,925 A | 2/1983 | Litman et al. |
| 4,427,836 A | 1/1984 | Kowalski et al. |
| 4,441,373 A | 4/1984 | White |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,534,356 A | 8/1985 | Papadakis |
| 4,537,861 A | 8/1985 | Elings et al. |
| 4,540,659 A | 9/1985 | Litman et al. |
| 4,552,458 A | 11/1985 | Lowne |
| 4,561,286 A | 12/1985 | Sekler et al. |
| 4,562,157 A | 12/1985 | Lowe et al. |
| 4,587,223 A * | 5/1986 | Soini et al. .................. 436/536 |
| 4,596,697 A | 6/1986 | Ballato |
| 4,614,723 A | 9/1986 | Schmidt et al. |
| 4,632,559 A | 12/1986 | Brunsting |
| 4,661,235 A | 4/1987 | Krull et al. |
| 4,698,262 A | 10/1987 | Schwartz et al. |
| 4,703,017 A | 10/1987 | Campbell et al. |
| 4,722,889 A | 2/1988 | Lee et al. |
| 4,776,944 A | 10/1988 | Janata et al. |
| 4,791,310 A | 12/1988 | Honig et al. |
| 4,818,710 A | 4/1989 | Sutherland et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,877,747 A | 10/1989 | Stewart |
| 4,877,965 A | 10/1989 | Dandliker et al. |
| 4,895,017 A | 1/1990 | Pyke et al. |
| 4,917,503 A | 4/1990 | Bhattacharjee |
| 4,923,819 A * | 5/1990 | Fernandez et al. .......... 436/518 |
| 4,973,670 A | 11/1990 | McDonald et al. |
| 4,992,385 A | 2/1991 | Godfrey |
| 5,003,178 A | 3/1991 | Livesay |
| 5,023,053 A | 6/1991 | Finlan |
| 5,035,863 A | 7/1991 | Finlan et al. |
| 5,051,162 A | 9/1991 | Kambara et al. |
| 5,055,265 A | 10/1991 | Finlan |
| 5,063,081 A | 11/1991 | Cozzette et al. |
| 5,064,619 A | 11/1991 | Finlan |
| 5,075,077 A | 12/1991 | Durley, III et al. |
| 5,076,094 A | 12/1991 | Frye et al. |
| 5,096,671 A | 3/1992 | Kane et al. |
| 5,114,676 A | 5/1992 | Leiner et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,152,758 A | 10/1992 | Kaetsu et al. |
| 5,156,953 A | 10/1992 | Litman et al. |
| 5,166,079 A | 11/1992 | Blackwood et al. |
| 5,182,135 A | 1/1993 | Giesecke et al. |
| 5,196,350 A | 3/1993 | Backman et al. |
| 5,221,454 A | 6/1993 | Manian et al. |
| 5,225,935 A | 7/1993 | Watanabe et al. |
| 5,235,238 A | 8/1993 | Nomura et al. |
| 5,242,828 A | 9/1993 | Bergström et al. |
| 5,268,306 A | 12/1993 | Berger et al. |
| 5,280,548 A | 1/1994 | Atwater et al. |
| 5,316,727 A | 5/1994 | Suzuki et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,369,717 A | 11/1994 | Attridge |
| 5,374,563 A | 12/1994 | Maule |
| 5,376,255 A | 12/1994 | Gumbrecht et al. |
| 5,387,503 A | 2/1995 | Selmer et al. |
| 5,415,842 A | 5/1995 | Maule |
| 5,418,136 A | 5/1995 | Miller et al. |
| 5,424,219 A | 6/1995 | Jirikowski |
| 5,424,841 A | 6/1995 | Van Gelder et al. |
| 5,432,057 A | 7/1995 | Litman et al. |
| 5,436,161 A | 7/1995 | Bergstrom et al. |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |
| 5,482,830 A | 1/1996 | Bogart et al. |
| 5,482,867 A | 1/1996 | Barrett et al. |
| 5,484,867 A | 1/1996 | Lichtenham et al. |
| 5,489,678 A | 2/1996 | Fodor et al. |
| 5,489,988 A | 2/1996 | Ackley et al. |
| 5,492,840 A | 2/1996 | Malmqvist et al. |
| 5,496,701 A | 3/1996 | Pollard-Knight |
| 5,504,013 A | 4/1996 | Senior |
| 5,508,171 A | 4/1996 | Walling et al. |
| 5,510,481 A | 4/1996 | Bednarski et al. |
| 5,512,131 A | 4/1996 | Kumar et al. |
| 5,514,559 A | 5/1996 | Markert-Hahn et al. |
| 5,514,785 A | 5/1996 | Van Ness et al. |
| 5,516,635 A | 5/1996 | Ekins et al. |
| 5,518,689 A | 5/1996 | Dosmann et al. |
| 5,518,883 A | 5/1996 | Soini |
| 5,527,711 A | 6/1996 | Tom-Moy et al. |
| 5,534,132 A | 7/1996 | Vreeke et al. |
| 5,554,541 A | 9/1996 | Malmqvist et al. |
| 5,569,608 A | 10/1996 | Sommer |
| 5,571,684 A | 11/1996 | Lawrence et al. |
| 5,589,401 A | 12/1996 | Hansen et al. |
| 5,591,581 A | 1/1997 | Massey et al. |
| 5,599,668 A | 2/1997 | Stimpson et al. |
| 5,618,888 A | 4/1997 | Choi et al. |
| 5,620,850 A | 4/1997 | Bamdad et al. |
| 5,658,443 A | 8/1997 | Yamamoto et al. |
| 5,663,213 A | 9/1997 | Jones et al. |
| 5,672,256 A | 9/1997 | Yee |
| 5,677,196 A | 10/1997 | Herron et al. |
| 5,700,636 A | 12/1997 | Sheiness et al. |
| 5,723,294 A | 3/1998 | Glass et al. |
| 5,726,064 A | 3/1998 | Robinson et al. |
| 5,731,147 A | 3/1998 | Bard et al. |
| 5,736,188 A | 4/1998 | Alcock et al. |
| 5,770,416 A | 6/1998 | Lihme et al. |
| 5,780,251 A | 7/1998 | Klainer et al. |
| 5,780,308 A | 7/1998 | Ching et al. |
| 5,795,543 A | 8/1998 | Poto et al. |
| 5,827,748 A | 10/1998 | Golden |
| 5,830,762 A | 11/1998 | Weindel |
| 5,832,165 A | 11/1998 | Reichert et al. |
| 5,834,226 A | 11/1998 | Maupin |
| 5,837,429 A | 11/1998 | Nohr et al. |
| 5,837,546 A | 11/1998 | Allen et al. |

| | | |
|---|---|---|
| 5,843,692 A | 12/1998 | Phillips et al. |
| 5,852,229 A | 12/1998 | Josse et al. |
| 5,876,944 A | 3/1999 | Kuo |
| 5,906,921 A | 5/1999 | Ikeda et al. |
| 5,910,447 A | 6/1999 | Lawrence et al. |
| 5,910,940 A | 6/1999 | Guerra |
| 5,922,537 A | 7/1999 | Ewart et al. |
| 5,922,550 A | 7/1999 | Everhart et al. |
| 5,943,129 A | 8/1999 | Hoyt et al. |
| 5,951,492 A | 9/1999 | Douglas et al. |
| 5,962,995 A | 10/1999 | Avnery |
| 6,004,530 A | 12/1999 | Sagner et al. |
| 6,008,892 A | 12/1999 | Kain et al. |
| 6,020,047 A | 2/2000 | Everhart |
| 6,027,904 A | 2/2000 | Devine et al. |
| 6,027,944 A | 2/2000 | Robinson et al. |
| 6,030,792 A | 2/2000 | Otterness et al. |
| 6,048,623 A | 4/2000 | Everhart et al. |
| 6,060,256 A | 5/2000 | Everhart et al. |
| 6,080,391 A | 6/2000 | Tsuchiya et al. |
| 6,084,683 A | 7/2000 | Bruno et al. |
| 6,087,184 A | 7/2000 | Magginetti et al. |
| 6,099,484 A | 8/2000 | Douglas et al. |
| 6,117,090 A | 9/2000 | Caillouette |
| 6,136,611 A | 10/2000 | Saaski et al. |
| 6,139,961 A | 10/2000 | Blankenship et al. |
| 6,151,110 A | 11/2000 | Markart |
| 6,165,798 A | 12/2000 | Brooks |
| 6,171,870 B1 | 1/2001 | Freitag |
| 6,174,646 B1 | 1/2001 | Hirai et al. |
| 6,177,281 B1 | 1/2001 | Manita |
| 6,180,288 B1 | 1/2001 | Everhart et al. |
| 6,200,820 B1 | 3/2001 | Hansen et al. |
| 6,221,238 B1 | 4/2001 | Grundig et al. |
| 6,221,579 B1 | 4/2001 | Everhart et al. |
| 6,234,974 B1 | 5/2001 | Catt et al. |
| 6,235,241 B1 | 5/2001 | Catt et al. |
| 6,241,863 B1 | 6/2001 | Monbouquette |
| 6,255,066 B1 | 7/2001 | Louderback |
| 6,261,779 B1 | 7/2001 | Barbera-Guillem et al. |
| 6,270,637 B1 | 8/2001 | Crismore et al. |
| 6,281,006 B1 | 8/2001 | Heller et al. |
| 6,287,783 B1 | 9/2001 | Maynard et al. |
| 6,287,871 B1 | 9/2001 | Herron et al. |
| 6,294,392 B1 | 9/2001 | Kuhr et al. |
| 6,306,665 B1 | 10/2001 | Buck et al. |
| D450,854 S | 11/2001 | Lipman et al. |
| 6,348,186 B1 | 2/2002 | Sutton et al. |
| 6,362,011 B1 | 3/2002 | Massey et al. |
| 6,368,873 B1 | 4/2002 | Chang et al. |
| 6,368,875 B1 | 4/2002 | Geisberg |
| 6,387,707 B1 | 5/2002 | Seul et al. |
| 6,391,558 B1 | 5/2002 | Henkens et al. |
| 6,396,053 B1 | 5/2002 | Yokoi |
| 6,399,295 B1 | 6/2002 | Kaylor et al. |
| 6,407,492 B1 | 6/2002 | Avnery et al. |
| 6,411,439 B2 | 6/2002 | Nishikawa |
| 6,413,410 B1 | 7/2002 | Hodges et al. |
| 6,436,722 B1 | 8/2002 | Clark et al. |
| 6,444,423 B1 | 9/2002 | Meade et al. |
| 6,448,091 B1 | 9/2002 | Massey et al. |
| 6,451,607 B1 | 9/2002 | Lawrence et al. |
| 6,461,496 B1 | 10/2002 | Feldman et al. |
| 6,468,741 B1 | 10/2002 | Massey et al. |
| 6,472,226 B1 | 10/2002 | Barradine et al. |
| 6,473,239 B1 | 10/2002 | Völcker et al. |
| 6,479,146 B1 | 11/2002 | Caruso et al. |
| 6,483,582 B2 | 11/2002 | Modlin et al. |
| 6,498,690 B2 | 12/2002 | Ramm et al. |
| 6,509,085 B1 | 1/2003 | Kennedy |
| 6,511,814 B1 | 1/2003 | Carpenter |
| 6,556,299 B1 | 4/2003 | Rushbrooke et al. |
| 6,566,508 B2 | 5/2003 | Bentsen et al. |
| 6,573,040 B2 | 6/2003 | Everhart et al. |
| 6,579,673 B2 | 6/2003 | McGrath et al. |
| 6,582,930 B1 | 6/2003 | Ponomarev et al. |
| 6,585,939 B1 | 7/2003 | Dapprich |
| 6,613,583 B1 | 9/2003 | Richter et al. |
| 6,617,488 B1 | 9/2003 | Springer et al. |
| 6,665,072 B2 | 12/2003 | Hoyt |
| 6,670,115 B1 | 12/2003 | Zhang |
| 6,720,007 B2 | 4/2004 | Walt et al. |
| 6,770,220 B1 | 8/2004 | Klimant |
| 6,787,368 B1 | 9/2004 | Wong et al. |
| 6,815,218 B1 | 11/2004 | Jacobson et al. |
| 6,867,851 B2 | 3/2005 | Blumenfeld et al. |
| 2001/0055776 A1 | 12/2001 | Greenwalt |
| 2002/0052048 A1 | 5/2002 | Stein et al. |
| 2002/0146754 A1 | 10/2002 | Kitawaki et al. |
| 2002/0164659 A1 | 11/2002 | Rao et al. |
| 2002/0167662 A1 | 11/2002 | Tanaami et al. |
| 2002/0177235 A1 | 11/2002 | Mabile et al. |
| 2003/0017615 A1 | 1/2003 | Sidwell et al. |
| 2003/0157727 A1 | 8/2003 | Nagano et al. |
| 2003/0178309 A1 | 9/2003 | Huang et al. |
| 2004/0014073 A1 | 1/2004 | Trau et al. |
| 2004/0130715 A1 | 7/2004 | Dosaka et al. |

FOREIGN PATENT DOCUMENTS

| | | |
|---|---|---|
| EP | 0617285 A2 | 9/1994 |
| EP | 0617285 A3 | 9/1994 |
| EP | 0745843 A2 | 12/1996 |
| EP | 0745843 A3 | 12/1996 |
| EP | 0859230 A1 | 8/1998 |
| EP | 1221616 A1 | 7/2002 |
| WO | WO 8804777 A1 | 6/1988 |
| WO | WO 9301308 A1 | 1/1993 |
| WO | WO 9709620 A1 | 3/1997 |
| WO | WO 99/30131 * | 6/1999 |
| WO | WO 9930131 A1 | 6/1999 |
| WO | WO 9964864 A1 | 12/1999 |
| WO | WO 0046839 A2 | 8/2000 |
| WO | WO 0046839 A3 | 8/2000 |
| WO | WO 0078917 A1 | 12/2000 |
| WO | WO 0150129 A2 | 7/2001 |
| WO | WO 0150129 A3 | 7/2001 |
| WO | WO 0163299 A1 | 8/2001 |
| WO | WO 0171344 A2 | 9/2001 |
| WO | WO 0198765 A1 | 12/2001 |
| WO | WO 0198785 A2 | 12/2001 |
| WO | WO 02077646 A1 | 10/2002 |
| WO | WO 02097408 A1 | 12/2002 |
| WO | WO 03005013 A1 | 1/2003 |
| WO | WO 03058246 A1 | 7/2003 |

OTHER PUBLICATIONS

Abstract of DE10024145A1, Nov. 22, 2001, Abstract only.

Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

Product Description for Fluorescence Microplate Assays from Molecular Probes, 112 pages.

U.S. Appl. No. 10/718,997, filed Nov. 21, 2003, Wei, et al., Extension Of The Dynamic Detection Range Of Assay Devices.

U.S. Appl. No. 10/719,916, filed Nov. 21, 2003, Xuedong Song, Method For Extending The Dynamic Detection Range Of Assay Devices.

U.S. Appl. No. 10/741,434, filed Dec. 19, 2003, Yang, et al., Laminated Assay Devices.

U.S. Appl. No. 10/742,589, filed Dec. 19, 2003, Yang, et al., Flow Control Of Electrochemcial-Based Assay Devices.

U.S. Appl. No. 10/742,590, filed Dec. 19, 2003, Yang, et al., Flow-Through Assay Devices.

U.S. Appl. No. 10/718,989, filed Nov. 21, 2003, Xuedong Song, Membrane-Based Lateral Flow Assay Devices That Utilize Phosphorescent Detection.

U.S. Appl. No. 10/718,996, filed Nov. 21, 2003, Ning Wei, Method Of Reducing The Sensitivity Of Assay Devices.

U.S. Appl. No. 10/836,093, filed Apr. 30, 2004, David S. Cohen, Optical Detection Systems.

U.S. Appl. No. 10/790,617, filed Mar. 1, 2004, Boga, et al., Assay Devices Utilizing Chemichronic Dyes.

Article—*Evaluation of a Time-Resolved Fluorescence Microscope Using a Phosphorescent Pt-Porphine Model System*, E. J. Hennink, R. de Hass, N. P. Verwoerd, and H. J. Tanke, Cytometry, vol. 24, 1996, pp. 312-320.

Article—*Inert Phosphorescent Nanospheres as Markers for Optical Assays*, Jens M. Kümer, Ingo Klimant, Christian Krause, Harald Preu, Werner Kunz, and Otto S. Wolfbeis, Bioconjugate Chem., vol. 12, No. 6, pp. 883-889.

Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.

Article—*Latex Immunoassays*, Leigh B. Bangs, Journal of Clinical Immunoassay, vol. 13, No. 3, 1990, pp. 127-131.

U.S. Appl. No. 10/035,013, filed Dec. 24, 2001, Kaylor, et al., Reading Device, Method, And System For Conducting Lateral Flow Assays.

U.S. Appl. No. 10/132,673, filed Apr. 25, 2002, Wei, et al., Internal Calibration System For Flow-Through Assays.

U.S. Appl. No. 10/132,421, filed Apr. 25, 2002, Song, et al., Polyelectrolytic Internal Calibration System Of A Flow-Through Assay.

U.S. Appl. No. 10/228,837, filed Aug. 27, 2002, Song, et al., Self-Calibration System For A Magnetic Binding Assay.

U.S. Appl. No. 10/228,838, filed Aug. 27, 2002, Song, et al., Fluidics-Based Assay Devices.

U.S. Appl. No. 10/228,836, filed Aug. 27, 2002, Song, et al., Membrane-Based Assay Devices.

U.S. Appl. No. 10/325,429, filed Dec. 19, 2002, Wei, et al., Self-Calibrated Flow-Through Assay Devices.

U.S. Appl. No. 10/308,926, filed Dec. 3, 2002, Yang, et al., Flow-Through Assay Devices.

U.S. Appl. No. 10/406,577, filed Apr. 3, 2003, Yang, et al., Assay Devices That Utilize Hollow Particles.

U.S. Appl. No. 10/325,614, filed Dec. 19, 2002, Wei, et al., Reduction Of The Hook Effect In Membrane-Based Assay Devices.

U.S. Appl. No. 10/406,631, filed Apr. 3, 2003, Wei, et al., Reduction Of The Hook Effect In Assay Devices.

\* cited by examiner

MEMBRANE-BASED ASSAY DEVICES THAT UTILIZE TIME-RESOLVED FLUORESCENCE

RELATED APPLICATIONS

The present application is a continuation-in-part of U.S. application Ser. No. 10/228,836, filed on Aug. 27, 2002 now U.S. Pat. No. 7,285,424.

BACKGROUND OF THE INVENTION

Assays have been developed that employ fluorescent labels to facilitate detection of the analyte. Fluorescence is generally the result of a three-stage process. In the first stage, energy is supplied by an external source, such as an incandescent lamp or a laser, and absorbed by the fluorescent compound, creating an excited electronic singlet state. In the second stage, the excited state exists for a finite time during which the fluorescent compound undergoes conformational changes and is also subject to a multitude of possible interactions with its molecular environment. During this time, the energy of the excited state is partially dissipated, yielding a relaxed state from which fluorescence emission originates. The third stage is the fluorescence emission stage wherein energy is emitted, returning the fluorescent compound to its ground state. The emitted energy is lower than its excitation energy (light or laser) and thus of a longer wavelength. This shift or difference in energy or wavelength allows the emission energy to be detected and isolated from the excitation energy.

Conventional fluorescence detection typically utilizes wavelength filtering to isolate the emission photons from the excitation photons, and a detector that registers emission photons and produces a recordable output, usually as an electrical signal or a photographic image. However, several problems exist with conventional fluorescent detection techniques. For instance, most biological fluids possess autofluorescence that can decrease detection accuracy. The assay device may also possess some autofluorescence. These interferences are enhanced by the small Stokes shifts of many conventional fluorescent labels, e.g., between 20 to 50 nanometers.

In response to some of the problems with conventional fluorescence detection techniques, a technique known as "time-resolved" fluorescence was developed. Time-resolved fluorescence involves exciting the fluorescent label with a short pulse of light, then waiting a certain time (e.g., between approximately 100 to 200 microseconds) after excitation before measuring the remaining long-lived fluorescent signal. In this manner, any short-lived background signals and scattered excitation radiation are eliminated. Although "time-resolved" techniques have been successfully employed in some types of assay devices, such as cuvette-based instruments, problems nevertheless remain in incorporating time-resolved techniques in other types of assay devices, such as membrane-based devices.

In particular, conventional time-resolved systems, such as those based on monochromators, involve very complex and expensive instruments. For example, a typical research-grade laboratory fluorimeter is a dual monochromator system, with one monochromator used to select the excitation wavelength and another monochromator used to select the detection wavelength. This level of complexity drastically increases the costs of the system and also requires a bulky, non-portable, and heavy instrument. In addition, conventional time-resolved systems are also problematic when used in conjunction with membrane-based assay devices. Specifically, in a membrane-based device, the concentration of the analyte is reduced because it is diluted by a liquid that can flow through the porous membrane. Unfortunately, background interference becomes increasingly problematic at such low analyte concentrations because the fluorescent intensity to be detected is relatively low. Because the structure of the membrane also tends to reflect the emitted light, the ability of the detector to accurately measure the fluorescent intensity of the labeled analyte is substantially reduced. In fact, the intensity of the emitted fluorescence signal is typically three to four orders of magnitude smaller than the excitation light reflected by the porous membrane.

As such, a need currently exists for a simple, inexpensive, and effective system for measuring the fluorescence in a membrane-based assay device.

SUMMARY OF THE INVENTION

In accordance with one embodiment of the present invention, a method for detecting the presence or quantity of an analyte residing in a test sample is disclosed that comprises:

i) providing a flow-through assay device that comprises a porous membrane in fluid communication with a fluorescent label, the fluorescent label having a fluorescence emission lifetime of greater than about 1 microsecond, the porous membrane defining a detection zone;

ii) contacting the fluorescent label with the test sample to form a mixture (e.g., solution, suspension, etc.);

iii) allowing the mixture to flow to the detection zone;

iv) placing a time-resolved fluorescence reader proximate to the detection zone, the fluorescence reader comprising a pulsed excitation source and a time-gated detector;

v) exciting the fluorescent label at the detection zone with the pulsed excitation source, wherein the excitation causes the fluorescent label to emit a detection signal; and vi) measuring the intensity of the detection signal with the time-gated detector.

The fluorescent label may include a lanthanide chelate of samarium, dysprosium, europium, terbium, or combinations thereof. Moreover, in some embodiments, the fluorescent label may have an emission lifetime of greater than about 10 microseconds, in some embodiments greater than about 50 microseconds, and in some embodiments, from about 100 to about 1000 microseconds. Likewise, the fluorescent label may have a Stokes shift of greater than about 50 nanometers, in some embodiments greater than about 100 nanometers, and in some embodiments, from about 250 to about 350 nanometers. If desired, the label may be used in conjunction with a microparticle that is modified with a specific binding member for the analyte.

The fluorescent reader can be used to accurately excite labels and detect fluorescence on a membrane-based assay device without requiring the use of expensive components, such as monochromators or narrow emission bandwidth optical filters. In one embodiment, for example, the pulsed excitation source is a silicon photodiode. The fluorescence reader may also contain timing circuitry (e.g., A/D convertors, microprocessors, amplifiers, dividers, crystal oscillators, transistors, flip-flop circuits, etc.) in communication with the pulsed excitation source and the time-gated detector to control signal pulsation and detection.

In accordance with another embodiment of the present invention, a method for detecting the presence or quantity of an analyte residing in a test sample is disclosed that comprises:

i) providing a flow-through assay device that comprises a porous membrane in fluid communication with a conjugated probe that contains a lanthanide chelate, the lanthanide chelate having a fluorescence emission lifetime of greater than about 50 microseconds and a Stokes shift greater than about 100 nanometers, the porous membrane defining a detection zone and a calibration zone; and ii) contacting the conjugated probe with the test sample to form a mixture;

iii) allowing the mixture to flow to the detection zone and the calibration zone;

iv) placing a time-resolved fluorescence reader proximate to the detection zone and the calibration zone, the fluorescence reader comprising a pulsed light-emitting diode and a time-gated detector that comprises a silicon photodiode, and combinations thereof;

v) exciting the lanthanide chelate at the detection zone and the calibration zone with the pulsed light-emitting diode, wherein the excitation causes the lanthanide chelate at the detection zone to emit a detection signal and the lanthanide chelate at the calibration zone to emit a calibration signal;

vi) measuring the intensity of the detection signal and the calibration signal with the time-gated detector;

vi) comparing the intensity of the detection signal to the calibration signal, wherein the amount of the analyte within the test sample is proportional to the intensity of the detection signal calibrated by the intensity of the calibration signal.

The fluorescent label at the detection zone may be excited simultaneously or separately from the fluorescent label at the calibration zone. Likewise, the detection signal and the calibration signal may also be measured simultaneously or separately.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
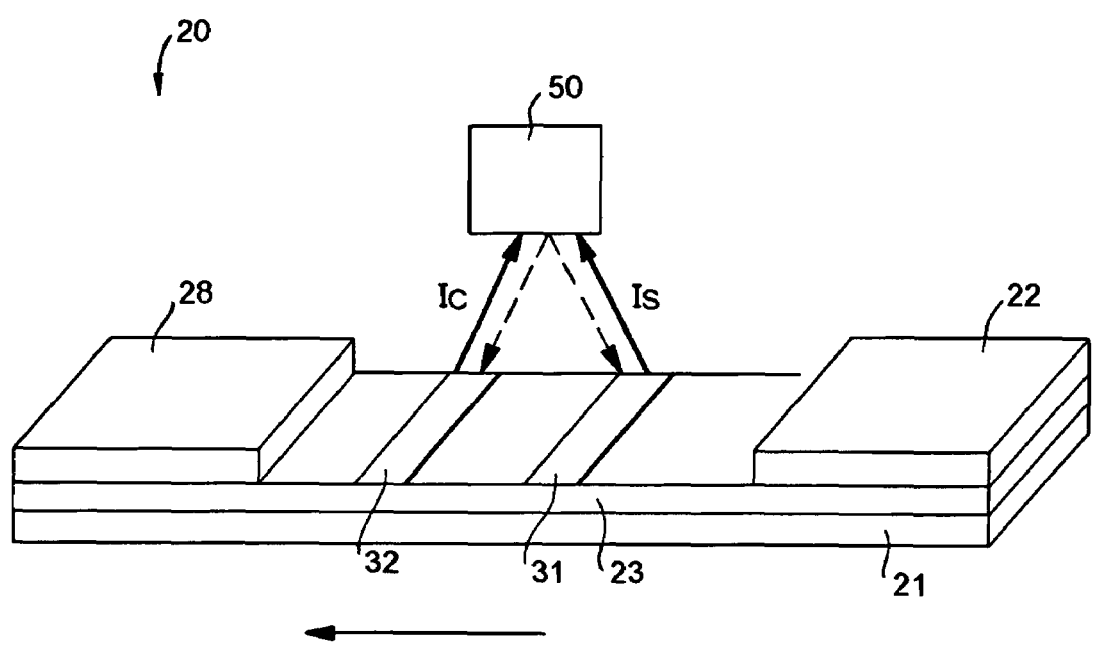
FIG. 1 is a perspective view of one embodiment of a membrane-based device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes can include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; C-reactive protein; lipocalins; IgE antibodies; vitamin B2 micro-globulin; glycated hemoglobin (Gly. Hb); cortisol; digitoxin; N-acetyl-procainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and U.S. Pat. No. 4,366,241 to Tom et al.

As used herein, the term "test sample" generally refers to a material suspected of containing the analyte. The test sample can be used directly as obtained from the source or following a pretreatment to modify the character of the sample. The test sample can be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The test sample can be pretreated prior to use, such as preparing plasma from blood, diluting viscous fluids, and the like. Methods of treatment can involve filtration, precipitation, dilution, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to a membrane-based assay device for detecting the presence or quantity of an analyte residing in a test sample. The device utilizes time-resolved fluorescence to detect the signals generated by excited fluorescent labels. Because the labels can have a long emission lifetime, background interference from many sources, such as scattered light and autofluorescence, can be practically eliminated during detection. In addition, the fluorescent reader used in the present invention can have a simple and inexpensive design. For instance, in one embodiment, the reader can utilize a pulsed light-emitting diode (LED) and a silicon photodiode to accurately excite labels and detect fluorescence on a membrane-based assay device without requiring the use of expensive components, such as monochromators or narrow emission band width optical filters.

Referring to FIG. 1, for instance, one embodiment of a flow-through assay device 20 that can be formed according to the present invention will now be described in more detail. As shown, the device 20 contains a porous membrane 23 optionally supported by a rigid material 21. In general, the porous membrane 23 can be made from any of a variety of materials through which the test sample is capable of passing. For example, the materials used to form the porous membrane 23 can include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; nylon membranes; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 can assist in promoting capillary action and fluid flow through the membrane 23.

To initiate the detection of an analyte within the test sample, a user may directly apply the test sample to a portion of the porous membrane 23 through which it can then travel. Alternatively, the test sample may first be applied to a sampling pad (not shown) that is in fluid communication with the porous membrane 23. Some suitable materials that can be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

In the illustrated embodiment, the test sample travels from the sampling pad (not shown) to a conjugate pad 22 that is placed in communication with one end of the sampling pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of an analyte within the test sample, labels are applied at various locations of the device 20. The labels may be used for both detection of the analyte and for calibration. Generally speaking, at least a portion of the labels used in the device 20 contain a fluorescent compound. In general, such fluorescent compounds can be fluorescent molecules, polymers, dendrimers, particles, and the like.

In accordance with the present invention, the fluorescent labels are configured to allow "time-resolved fluorescence detection." Time-resolved fluorescence involves exciting the fluorescent label with a short pulse of light, then typically waiting a certain time (e.g., between approximately 100 to 200 microseconds) after excitation before measuring the remaining long-lived fluorescent signal. In this manner, any short-lived fluorescent background signals and scattered excitation radiation are eliminated. This ability to eliminate much of the background signals can result in sensitivities that are 2 to 4 orders greater than conventional fluorescence. Thus, time-resolved fluorescence detection is designed to reduce background signals from the emission source or from scattering processes (resulting from scattering of the excitation radiation) by taking advantage of the fluorescence characteristics of certain fluorescent materials.

The selection criteria of particularly desired labels for time-resolved fluorescence include a relatively long emission lifetime. As indicated above, this is desired so that the label emits its signal well after any short-lived background signals dissipate. Furthermore, a long fluorescence lifetime makes it possible to use low-cost circuitry for time-gated fluorescence measurements. For example, fluorescent labels used in the present invention may have a fluorescence lifetime of greater than about 1 microsecond, in some embodiments greater than about 10 microseconds, in some embodiments greater than about 50 microseconds, and in some embodiments, from about 100 microseconds to about 1000 microseconds. In addition, the fluorescent label may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of the fluorescent label to remain far apart from its emission wavelengths and is desirable because a large difference between excitation and emission wavelengths makes it easier to eliminate the reflected excitation radiation from the emitted signal. Further, a large Stokes shift also minimizes interference from fluorescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the fluorescent labels have a Stokes shift of greater than about 50 nanometers, in some embodiments greater than about 100 nanometers, and in some embodiments, from about 250 to about 350 nanometers.

One type of fluorescent compound that has both a relatively long emission lifetime and relatively large Stokes shift are lanthanide chelates of samarium (Sm (III)), dysprosium (Dy (III)), europium (Eu (III)), and terbium (Tb (III)). Such chelates can exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy can be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein.

Also, the fluorescence of europium chelates is long-lived, with lifetimes of about 100 to about 1000 microseconds, as compared to about 1 to about 100 nanoseconds for other fluorescent labels. In addition, these chelates have a very narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. Nos. 6,030,840 to Mullinax, et al.; U.S Pat. No. 5,585, 279 to Davidson; U.S Pat. No. 5,573,909 to Singer, et al.; U.S Pat. No. 6,242,268 to Wieder, et al.; and U.S Pat. No. 5,637, 509 to Hemmila, et al., which are incorporated herein in their entirety by reference thereto for all purposes.

The fluorescent labels may be used in a variety of ways to form a probe. For example, the labels may be used alone to form probes. Alternatively, the labels may be used in conjunction with polymers, liposomes, dendrimers, and other micro- or nano-scale structures to form probes. In addition, the labels may be used in conjunction with microparticles (sometimes referred to as "beads" or "microbeads") to form probes. For instance, naturally occurring microparticles, such as nuclei, mycoplasma, plasmids, plastids, mammalian cells (e.g., erythrocyte ghosts), unicellular microorganisms (e.g., bacteria), polysaccharides (e.g., agarose), silica, glass, cellulose-based particles, and the like, can be used. Further, synthetic microparticles may also be utilized. For example, in one embodiment, latex microparticles that are labeled with a fluorescent or colored dye are utilized. Although any latex microparticle may be used in the present invention, the latex microparticles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and the like, or an aldehyde, carboxyl, amino, hydroxyl, or hydrazide derivative thereof. Other suitable microparticles may be described in U.S. Pat. Nos. 5,670,381 to Jou, et al. and U.S Pat. No. 5,252,459 to Tarcha, et al., which are incorporated herein in their entirety by reference thereto for all purposes.

In some embodiments, the microparticles may be magnetic. Generally, a material is considered "magnetic" if it is influenced by the application of a magnetic field, such as, for example, if it is attracted or repulsed or has a detectable magnetic susceptibility or induction. For instance, some examples of suitable magnetically responsive materials that can be used to impart magnetic properties to a probe include, but are not limited to, paramagnetic materials, superparamagnetic materials, ferromagnetic materials, ferrimagnetic materials, and metamagnetic materials. Specific examples are metals such as iron, nickel, cobalt, chromium, manganese, and the like; lanthanide elements such as neodymium, erbium, and the like; alloys such as magnetic alloys of aluminum, nickel, cobalt, copper and the like; oxides such as ferric oxide ($Fe_3O_4$), ferrous oxide ($Fe_2O_3$), chromium oxide ($CrO_2$), cobalt oxide (CoO), nickel oxide ($NiO_2$), manganese oxide ($Mn_2O_3$) and the like; composite materials such as ferrites and the like; and solid solutions such as magnetite with ferric oxide and the like.

When particles are utilized, such as described above, the mean diameter of the particles may generally vary as desired depending on factors such as the type of particle chosen, the pore size of the membrane, and the membrane composition. For example, in some embodiments, the mean diameter of the particulate labels can range from about 0.01 microns to about 1,000 microns, in some embodiments from about 0.01 microns to about 100 microns, and in some embodiments, from about 0.01 microns to about 10 microns. In one particular embodiment, the particles have a mean diameter of from about 0.1 to about 2 microns. Generally, the particles are substantially spherical in shape, although other shapes including, but not limited to, plates, rods, bars, irregular shapes, etc., are suitable for use in the present invention. As will be appreciated by those skilled in the art, the composition, shape, size, and/or density of the particles may widely vary.

In some instances, it is desired to modify the probes in some manner so that they are more readily able to bond to the analyte. In such instances, the probes can be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members can include antigens, haptens, aptamers, antibodies, and complexes thereof, including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin, biotin and streptavidin, antibody-binding proteins (such as protein A or G) and antibodies, carbohydrates and lectins, complementary nucleotide sequences (including label and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

The specific binding members can generally be attached to the probes using any of a variety of well-known techniques. For instance, covalent attachment of the specific binding members to the probes (e.g., labeled microparticles) can be accomplished using carboxylic, amino, aldehyde, bromoacetyl, iodoacetyl, thiol, epoxy and other reactive or linking functional groups, as well as residual free radicals and radical cations, through which a protein coupling reaction can be accomplished. A surface functional group can also be incorporated as a functionalized co-monomer because the surface of the microparticle can contain a relatively high surface concentration of polar groups. In addition, although microparticle labels are often functionalized after synthesis, in certain cases, such as poly(thiophenol), the microparticles are capable of direct covalent linking with a protein without the need for further modification. For example, in one embodiment, the first step of conjugation is activation of carboxylic groups on the particle surface using carbodiimide.

In the second step, the activated carboxylic acid groups are reacted with an amino group of an antibody to form an amide bond. The activation and/or antibody coupling can occur in a buffer, such as phosphate-buffered saline (PBS) (e.g., pH of 7.2) or 2-(N-morpholino) ethane sulfonic acid (MES) (e.g., pH of 5.3). As shown, the resulting particles can then be blocked with ethanolamine, for instance, to form the label conjugate. Besides covalent bonding, other attachment techniques, such as physical adsorption, may also be utilized in the present invention.

In general, a variety of flow-through assay devices may be constructed according to the present invention for use in conjunction with a time-resolved fluorescence detection system. In this regard, various embodiments of the present invention will now be described in more detail. It should be understood, however, that the embodiments discussed below are only exemplary, and that other embodiments are also contemplated by the present invention. For instance, referring again to FIG. 1, one system for detecting the presence of an analyte within a test sample is schematically illustrated. Initially, a test sample containing an analyte is applied to the sampling pad (not shown). From the sampling pad, the test sample can then travel to the conjugate pad 22, where the analyte mixes with probes to form analyte complexes. In one embodiment, for example, the probes are formed from microparticles that are dyed with a lanthanide chelate label, such as described above, and bound to a specific binding member for the analyte of interest. Moreover, because the conjugate pad 22 is in fluid communication with the porous membrane 23, the complexes can migrate from the conjugate pad 22 to a detection zone 31 present on the porous membrane 23.

The detection zone 31 may contain an immobilized capture reagent that is generally capable of forming a chemical or physical bond with the probes. For example, in some embodiments, the binders can contain a biological capture reagent. For example, in some embodiments, the capture reagent may be a biological capture reagent. Such biological capture reagents are well known in the art and can include, but are not limited to, antigens, haptens, antibodies, protein A or G, avidin, streptavidin, secondary antibodies, and complexes thereof. In many cases, it is desired that these biological capture reagents are capable of binding to a specific binding member (e.g., antibody) present on microparticles. In addition, it may also be desired to utilize various non-biological materials for the binders. For instance, in some embodiments, the binders can include a polyelectrolyte that can bind to the uncaptured probes. The polyelectrolytes can have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and the like. In one particular embodiment, CelQuat® SC-230M or H-100 (available from National Starch & Chemical, Inc.), which are cellulosic derivatives containing a quaternary ammonium water-soluble monomer, can be utilized. Moreover, some suitable examples of polyelectrolytes having a net negative charge include, but are not limited to, polyacrylic acids, such as poly(ethylene-co-methacrylic acid, sodium salt), and the like. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

These capture reagents serve as stationary binding sites for probe conjugate/analyte complexes. In some instances, the analytes, such as antibodies, antigens, etc., have two binding sites. Upon reaching the detection zone 31, one of these binding sites is occupied by the specific binding member of the complexed probes. However, the free binding site of the analyte can bind to the immobilized capture reagent. Upon being bound to the immobilized capture reagent, the complexed probes form a new ternary sandwich complex.

The detection zone 31 may generally provide any number of distinct detection regions so that a user can better determine the concentration of a particular analyte within a test sample. Each region may contain the same capture reagents, or may contain different capture reagents for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions can be disposed in the form of lines in a direction that is substantially parallel to the flow of the test sample through the assay device.

Although the detection zone 31 may indicate the presence of an analyte, it is often difficult to determine the relative concentration of the analyte within the test sample using solely a detection zone 31. Thus, the assay device 20 may also include a calibration zone 32. In this embodiment, the calibration zone 32 is formed on the porous membrane 23 and is positioned downstream from the detection zone 31. The calibration zone 32 is provided with a capture reagent that is capable of binding to any remaining uncaptured probes that pass through the length of the membrane 23. In particular, upon being contacted with the test sample, any uncaptured probes that do not bind to the analyte migrate through the detection zone 31 and enter the calibration zone 32 of the porous membrane 23. At the calibration zone 32, these uncaptured probes then bind to the capture reagents. The capture reagents utilized in the calibration zone 32 may be the same or different than the capture reagents used in the detection zone 31. Moreover, similar to the detection zone 31, the calibration zone 32 may also provide any number of distinct calibration regions in any direction so that a user can better determine the concentration of a particular analyte within a test sample. Each region may contain the same capture reagents, or may contain different capture reagents for capturing different fluorescent labels.

The calibration regions may be pre-loaded on the porous membrane 23 with different amounts of the binder so that a different signal intensity is generated by each calibration region upon migration of the uncaptured probes. The overall amount of binder within each calibration region can be varied by utilizing calibration regions of different sizes and/or by varying the concentration or volume of the binder in each calibration region. If desired, an excess of probe molecules can be employed in the assay device 20 so that each calibration region reaches its full and predetermined potential for signal intensity. That is, the amount of uncaptured probes that are deposited upon calibration regions are predetermined because the amount of the binder employed on the calibration regions is set at a predetermined and known level.

Once captured, the fluorescence signal of the probes at the detection and calibration zones 31 and 32 can be measured using a time-resolved fluorescence reader 50. For example, in this embodiment, the fluorescence reader 50 is constructed to emit pulsed light simultaneously onto the detection and calibration zones 31 and 32. The reader 50 may also simultaneously receive the fluorescent signal from the excited labels at the detection and calibration zones 31 and 32. Alternatively, the fluorescence reader 50 may be constructed to successively emit pulsed light onto the detection zone 31 and the calibration zone 32. In addition, a separate fluorescence reader (not shown) may also be used to measure the fluorescent signal at the calibration zone 32.

The construction of the fluorescence reader 50 may generally vary depending on a variety of factors, such as cost, the level of accuracy required, the nature and concentration of the analyte of interest, and the like. Typically, the fluorescence reader 50 utilizes one or more pulsed excitation sources and photodetectors that are in communication with each other and other optional components, such as optical filters. The use of pulsed excitation and time-gated detection, optionally combined with optical filters, allows for specific detection of the fluorescence from only the fluorescent label, rejecting emission from other species present in the sample that are typically shorter-lived.

Figure 2:
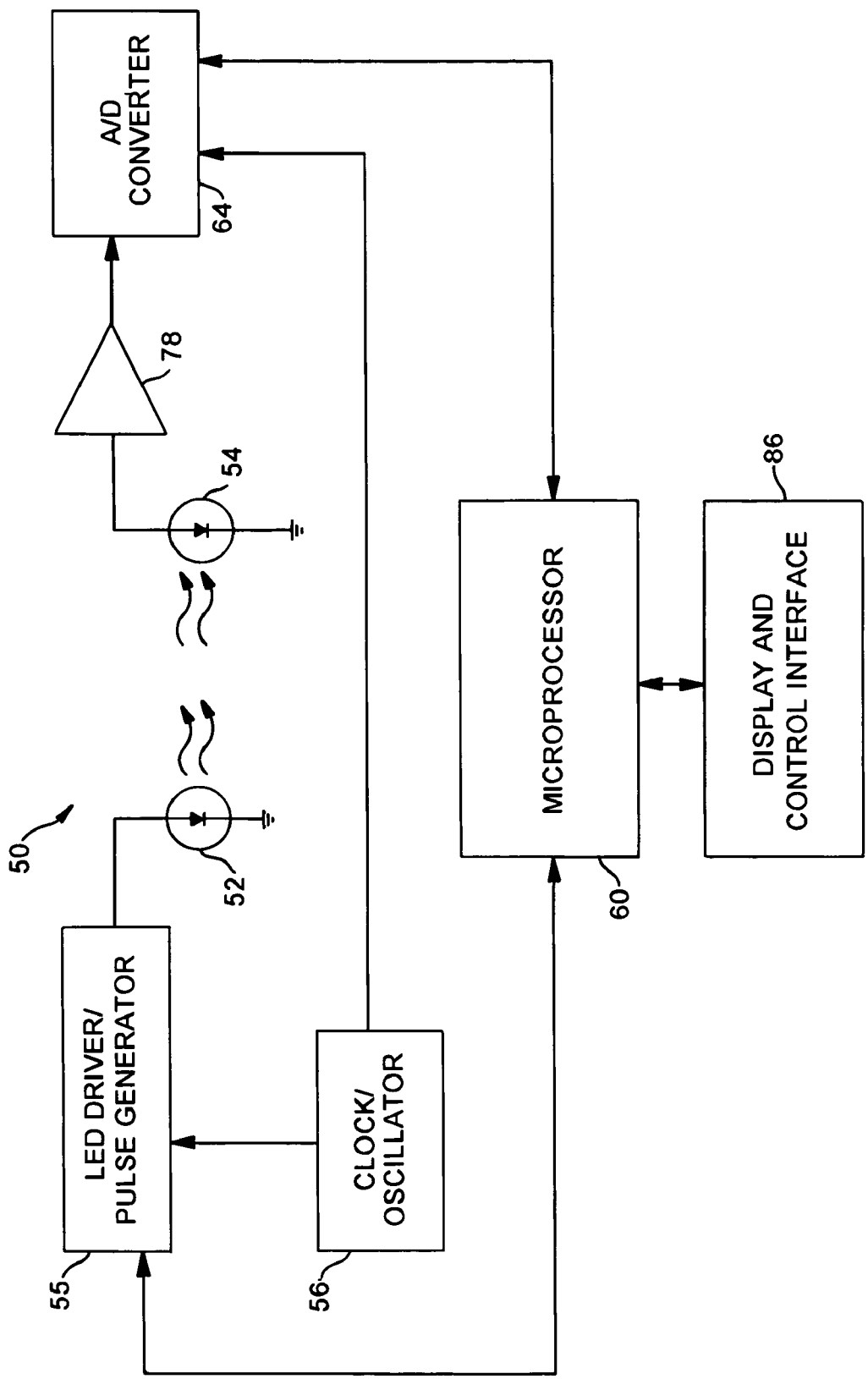
FIG. 2 is a schematic diagram of one embodiment of a time-resolved fluorescence reader that may be used in the present invention, including representative electronic components thereof.

For instance, referring to FIG. 2, one embodiment of an exemplary fluorescence reader 50 is shown that includes an excitation source 52 and a detector 54. Various excitation sources 52 may be used in the present invention, including, for example, light emitting diodes (LED), flashlamps, as well as other suitable sources. Excitation illumination may also be multiplexed and/or collimated; for example, beams of various discrete frequencies from multiple coherent sources (e.g., lasers) can be collimated and multiplexed using an array of dichroic mirrors. Further, illumination may be continuous or pulsed, or may combine continuous wave (CW) and pulsed illumination where multiple illumination beams are multiplexed (e.g., a pulsed beam is multiplexed with a CW beam), permitting signal discrimination between fluorescence induced by the CW source and fluorescence induced by the pulsed source. For example, gallium arsenide LED diodes (e.g., aluminum gallium arsenide red diodes, gallium phosphide green diodes, gallium arsenide phosphide green diodes, or indium gallium nitride violet/blue/ultraviolet (UV) diodes) can be used as an illumination source. One commercially available example of a suitable UV LED excitation diode suitable for use in the present invention is Model NSHU550E (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

Further, examples of suitable detectors 54 that can be used in the present invention include, but not limited to, photomultiplier devices; photodiodes, such as avalanche photodiodes, silicon photodiodes, etc.; high speed, linear charge-coupled devices (CCD), CID devices, or CMOS based imagers; and the like. In one embodiment, the fluorescent system utilizes a silicon photodiode for fluorescent detection. Silicon photodiodes are advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into a system for use in membrane-based devices. If silicon photodiodes are used, then the wavelength range of the fluorescent emission should be within their range of sensitivity, which is 400 to 1100 nanometers. Another detector option is a CdS (cadmium sulfide) photoconductive cell, which has the advantage of having a spectral sensitivity similar to that of human vision (photopic curve) that may make rejection of the reflected excitation radiation easier.

Optionally, optical filters (not shown) may be disposed adjacent to the excitation source 52 and the detector 54. The optical filters may have high transmissibility in the excitation wavelength range(s) and low transmissibility in one or more undesirable wavelength band(s) to filter out undesirable wavelengths from the excitation source. Undesirable wavelength ranges generally include those wavelengths that produce detectable sample autofluoresence and/or are within about 25 to about 100 nanometers of excitation maxima wavelengths and thus are potential sources of background noise from scattered excitation illumination. Several examples of optical filters that may be utilized in the present invention include, but are not limited to, dyed plastic resin or gelatin filters, dichroic filters, thin multi-layer film interference filters, plastic or glass filters, epoxy or cured transparent resin filters. In one embodiment, the detector and/or excitation source may be embedded or encapsulated within the filter. Although optical filters may be utilized, one beneficial aspect of the present invention is that such filters are often not required as a result of time-resolving. Specifically, due to the delay in fluorescence emission, emission bandwidth filters may not be required to filter out any short-lived fluorescence emitted by the excitation source.

Referring again to FIG. 2, various timing circuitry is also used to control the pulsed excitation of the excitation source 52 and the measurement of the emitted fluorescence. For instance, in the illustrated embodiment, a clock source 56 (e.g., a crystal oscillator) is employed to provide a controlled frequency source to other electronic components in the fluorescence reader 50. In this particular embodiment, for instance, the oscillator 56 may generate a 20 MHz signal, which is provided to an LED driver/pulse generator 55 and to an A/D converter 64. The clock signal from oscillator 56 to A/D converter 64 controls the operating speed of A/D converter 64. It should be appreciated that a frequency divider may be utilized in such respective signal paths if the operating frequency of A/D converter 64 or if the desired frequency of the clock input to LED driver/pulse generator 55 is different than 20 MHz. Thus, it should be appreciated that the signal from oscillator 56 may be modified appropriately to provide signals of a desired frequency. In some embodiments, a signal from oscillator 56 may also be provided to microprocessor 60 to control its operating speed. Additional frequency dividers may be utilized in other signal paths in accordance with the present invention.

Microprocessor 60 provides control input to pulse generator 55 such that the 20 MHz signal from oscillator 56 is programmably adjusted to provide a desired pulse duration and repetition rate (for example, a 1 kHz source with a 50% duty cycle). The signal from pulse generator 55 may then be provided to the excitation source 52, controlling its pulse repetition rate and duty cycle of illumination. In some embodiments, a transistor may be provided in the signal path to excitation source 52, thus providing a switching means for effecting a pulsed light signal at excitation source 52.

As described above, the pulsed light excites fluorescent labels associated with the subject assay devices. After the desired response time (e.g., about 100 to about 200 microseconds), the detector 54 detects the fluorescence signal emitted by the excited fluorescent labels and generates an electric current representative thereof. This electric current may then be converted to a voltage level by a high-speed transimpedance preamplifier 78, which may be characterized by a relatively low settling time and fast recovery from saturation. The output of the preamplifier 78 may then be provided to the data input of A/D converter 64. Additional amplifier elements (such as a programmable gain amplifier) may be employed in the signal path after preamplifier 78 and before A/D converter 64 to yield a signal within an appropriate voltage range at the trailing edge of the excitation pulse for provision to the A/D converter 64. A/D converter 64 may be a high-speed converter that has a sample rate sufficient to acquire many points within the fluorescence lifetime of the subject fluorescent labels. The gain of the preamplifier 78 may be set such that data values drop below the maximum A/D count (e.g., 2047 for a 12-bit converter) on the trailing edge of the excitation pulse. Data within the dynamic range of A/D converter 64 would then be primarily representative of the desired fluorescence signal. If the sample interval is short compared with the rise-time and fall-time of the excitation pulse, then the gain of preamplifier 78 may be set to ensure that signal values within the upper ½ or ¾ of the dynamic range of A/D converter 78 correspond to the trailing edge of the emission pulse.

A/D converter 64 samples the signal from preamplifier 78 and provides it to the microprocessor 60 where software instruction is configured for various processing of the digital signal. An output from the microprocessor 60 is provided to the A/D converter 64 to further control when the detected fluorescence signal is sampled. Control signals to preamplifier 78 (not shown) and to A/D converter 64 may be continuously modified to achieve the most appropriate gain, sampling interval, and trigger offset. It should be appreciated that although the A/D converter 64 and the microprocessor 60 are depicted as distinct components, commercially available chips that include both such components in a single module may also be utilized in the present invention. After processing, the microprocessor 60 may provide at least one output indicative of the fluorescence levels detected by the detector 54. One such exemplary output is provided to a display 86, thus providing a user with a visual indication of the fluorescence signal generated by the label. Display 86 may provide additional interactive features, such as a control interface to which a user may provide programmable input to microprocessor 60.

Figure 3:
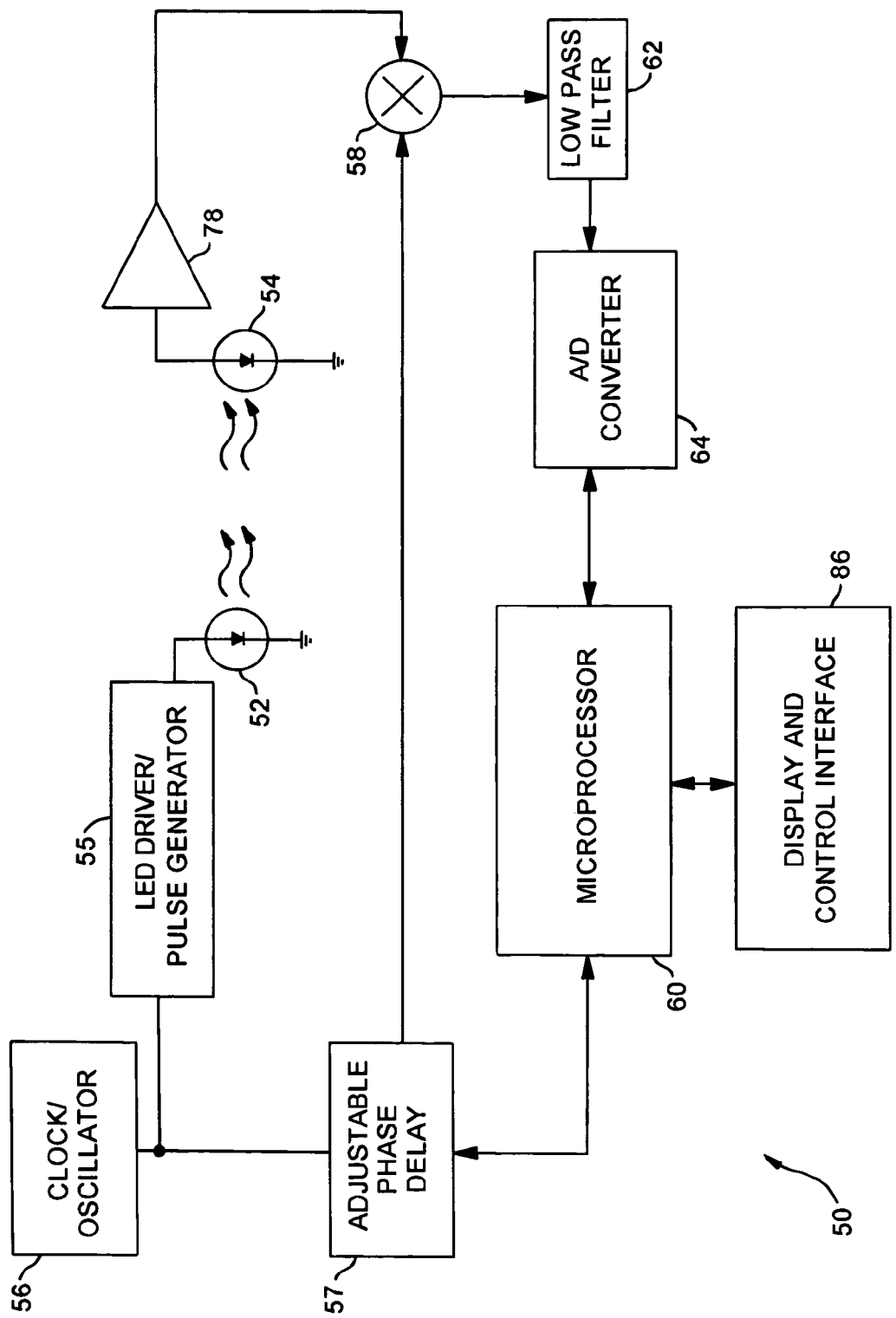
FIG. 3 is a schematic diagram of another embodiment of a time-resolved fluorescence reader that may be used in the present invention, including representative electronic components thereof.

Yet another embodiment of representative specific electronic components for use in a fluorescence reader 50 is illustrated in FIG. 3. Many of the components in FIG. 3 are analogous to those of FIG. 2 and so the same reference characters are used in such instances. For example, one difference in the reader 50 of FIG. 3 as compared to that of FIG. 2 is the generation of a gate signal at phase delay module 57. A control signal from microprocessor 60 is provided to phase delay module 57 to program the effective phase shift of a clock signal provided thereto. This shifted clock signal (also referred to as a gate signal) is then provided to a mixer 58 where such signal is multiplied by the periodic detector signal received by the detector 54 and passed through preamplifier 78. The resulting output of mixer 58 is then sent through a low-pass filter 62 before being provided to A/D converter 64. A/D converter 64 can then measure the output of low-pass filter 62 to obtain a measurement of the fluorescence during intervals defined by the gate signal.

Figure 4:
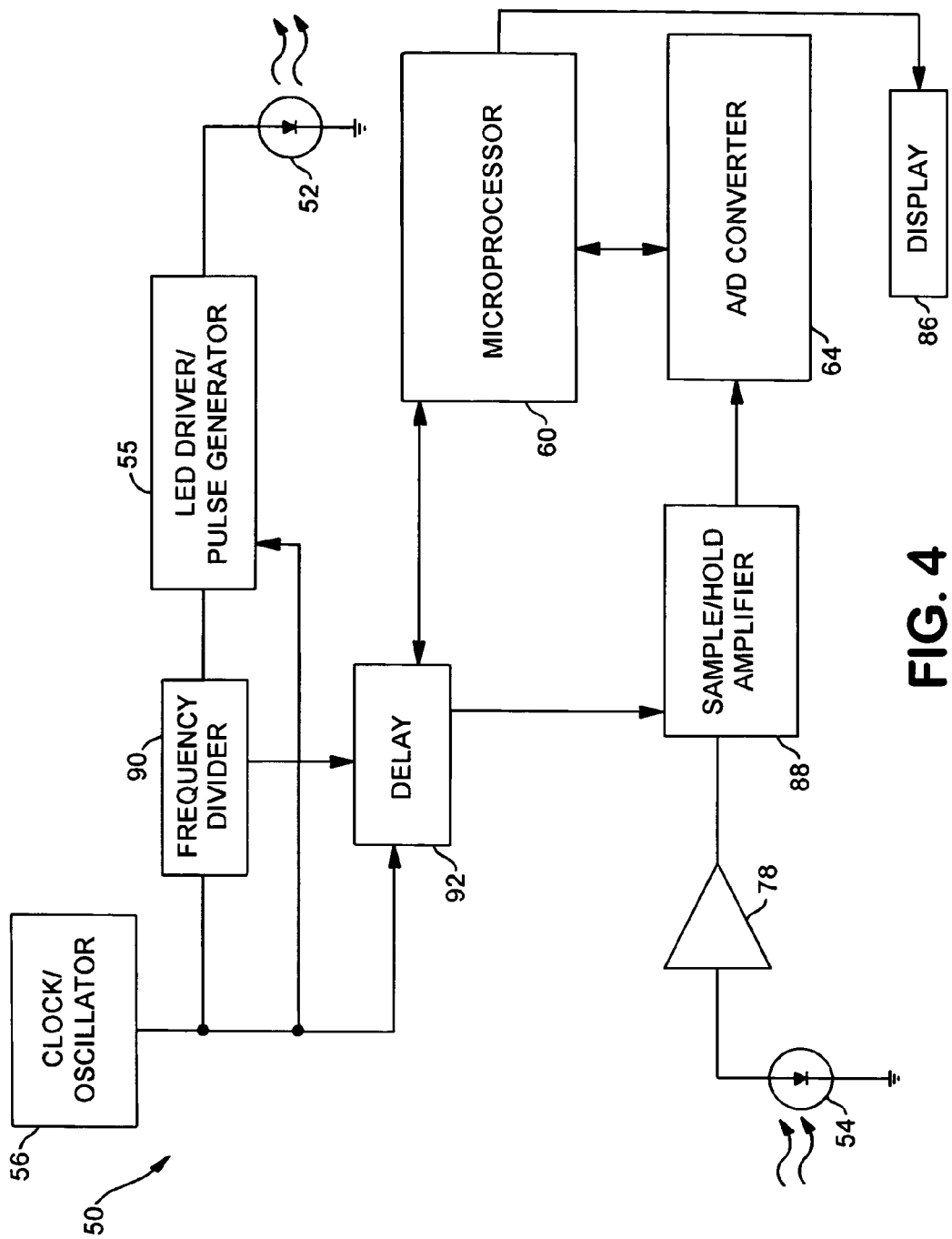
FIG. 4 is a schematic diagram of still another embodiment of a time-resolved fluorescence reader that may be used in the present invention, including representative electronic components thereof.

Still further alternative features for an exemplary fluorescence reader embodiment 50 are illustrated in FIG. 4. For instance, a sample/hold amplifier 88 (also sometimes referred to as a track-and-hold amplifier) is shown that captures and holds a voltage input signal at specific points in time under control of an external signal. A specific example of a sample/hold amplifier for use with the present technology is a SHC5320 chip, such as those sold by Burr-Brown Corporation. The sample/hold amplifier external control signal in the embodiment of FIG. 4 is received from a delay circuit 92, which may, for instance, be digital delay circuit that derives a predetermined delay from the clock using counters, basic logic gates, and a flip-flop circuit. Delay circuit 92 receives a clock signal from oscillator 56 and an enable signal from frequency divider 90, which simply provides a periodic signal at a reduced frequency level than that generated at oscillator 56. Delay circuit 92 may also receive a control input from microprocessor 60 to enable programmable aspects of a delay to ensure proper sampling at sample/hold amplifier 88. The delayed pulse control signal from delay circuit 92 to sample/hold amplifier 88 thus triggers acquisition of the fluorescence signal from the detector 54 at preset time intervals after the excitation source 52 has turned off.

Regardless of the construction of the reader 50 utilized, the amount of the analyte can be ascertained by correlating the emitted fluorescence signal, $I_s$, of the labels captured at the detection zone 31 to a predetermined analyte concentration. In some embodiments, the intensity signal, $I_s$, may also be compared with the emitted fluorescence intensity signal, $I_c$, of the labels captured at the calibration zone 32. The fluorescence intensity signal $I_s$, can be compared to the fluorescence intensity signal $I_c$. In this embodiment, the total amount of the labels at the calibration zone 32 is predetermined and known and thus can be used for calibration purposes. For example, in some embodiments (e.g., sandwich assays), the amount of analyte is directly proportional to the ratio of $I_s$ to $I_c$. In other embodiments (e.g., competitive assays), the amount of analyte is inversely proportional to the ratio of $I_s$ to $I_c$. Based upon the intensity range in which the detection zone 31 falls, the general concentration range for the analyte may be determined. As a result, calibration and sample testing may be conducted under approximately the same conditions at the same time, thus providing reliable quantitative or semi-quantitative results, with increased sensitivity.

If desired, the ratio of $I_s$ to $I_c$ may be plotted versus the analyte concentration for a range of known analyte concentrations to generate a calibration curve. To determine the quantity of analyte in an unknown test sample, the signal ratio may then be converted to analyte concentration according to the calibration curve. It should be noted that alternative mathematical relationships between $I_s$ and $I_c$ may be plotted versus the analyte concentration to generate the calibration curve. For example, in one embodiment, the value of $I_s/(I_s+I_c)$ may be plotted versus analyte concentration to generate the calibration curve.

As indicated above, sandwich formats, competitive formats, and the like, may be utilized for the device 20. Sandwich assay formats typically involve mixing the test sample with antibodies to the analyte. These antibodies are mobile and linked to a label or label, such as dyed latex, a colloidal metal sol, or a radioisotope. This mixture is then contacted with a chromatographic medium containing a band or zone of immobilized antibodies to the analyte. The chromatographic medium is often in the form of a strip resembling a dipstick. When the complex of the analyte and the labeled antibody reaches the zone of the immobilized antibodies on the chromatographic medium, binding occurs and the bound labeled antibodies are localized at the zone. This indicates the presence of the analyte. This technique can be used to obtain quantitative or semi-quantitative results. Some examples of such sandwich-type assays are described by U.S. Pat. Nos. 4,168,146 to Grubb, et al. and U.S Pat. No. 4,366,241 to Tom, et al., which are incorporated herein in their entirety by reference thereto for all purposes.

In a competitive assay, the label is generally a labeled analyte or analyte-analogue that competes for binding of an antibody with any unlabeled analyte present in the sample. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., U.S Pat. No. 4,442,204 to Liotta, and U.S Pat. No. 5,208,535 to Buechler, et al., which are incorporated herein in their entirety by reference thereto for all purposes. Various other device configurations and/or assay formats are also described in U.S. Pat. Nos. 5,395,754 to Lambotte, et al.; U.S Pat. No. 5,670,381 to Jou, et al.; and U.S Pat. No. 6,194,220 to Malick, et al., which are incorporated herein in their entirety by reference thereto for all purposes.

Although various embodiments of device configurations have been described above, it should be understood, that a device of the present invention may generally have any configuration desired, and need not contain all of the components described above.

The present invention may be better understood with reference to the following examples.

EXAMPLE 1

The ability to form conjugated fluorescent probe particles for use in a membrane-based device was demonstrated. 500 microliters of 0.5% carboxylated europium chelate encapsulated particles (0.20 microns, EU-P particles, obtained from Molecular Probes, Inc.) were washed with 100 microliters of a PBS buffer (0.1 molar). 40 microliters of the washed particles were then applied with 3 milligrams of carbodiimide (from Polysciences, Inc.). The mixture was allowed to react at room temperature (RT) for 30 minutes on a shaker. The activated particles were then washed twice with a borate buffer through centrifugation. The activated particles were again re-suspended in 200 microliters of a borate buffer through a 2-minute bath sonication.

Thereafter, 30 microliters of C-reactive protein (CRP) (4.9 milligrams per milliliter, Mab1 A58110228P, obtained from BiosPacific, Inc. of Emeryville, Calif., was added to the activated particles. The reaction mixture was allowed to react at room temperature on a shaker for 2.5 hours. The activated particles were then collected and incubated in 0.25 milliliters of 0.25 molar ethanolamine under gentle shaking for 30 minutes. The particles were then washed twice with PBS. The particles were then probe-sonicated in PBS three times for 10 seconds under an ice bath and stored at 4° C.

EXAMPLE 2

The excitation and emission spectra of the conjugated probe particles formed in Example 1 was determined using a conventional FluoroLog III spectrofluorometer (purchased from Horiba Group) using an excitation wavelength of 370 nanometers and an emission wavelength of 615 nanometers.

Figure 5:
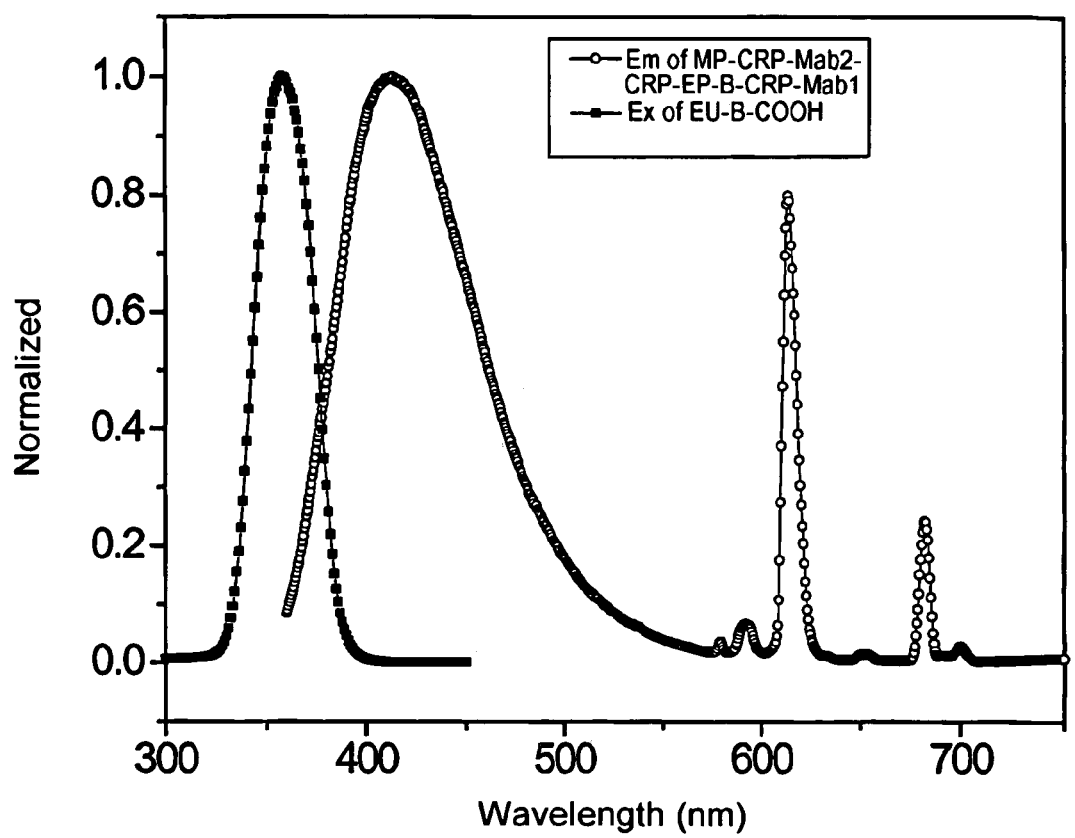
FIG. 5 is a graph of normalized excitation and emission spectra for the results obtained in Example 2.

The results are shown in FIG. 5. As shown, the excitation and emission spectra of the probe particles were similar to the excitation and emission spectra of the unconjugated probe particles, except the relative intensity of the 430 nanometer peak to 615 nanometer peak for the conjugate was higher. The conjugated probe particles had a strong excitation peak at around 355 nanometers and two strong emission peaks at 430 and 615 nanometers. The emission peak at 430 nanometers was believed to originate from the ligand while the peak at 615 nanometers was believed to be from d-d transition of europium metal ion through energy transfer from ligand to the europium metal center.

EXAMPLE 3

The ability to form a membrane-based assay was demonstrated. Initially, Millipore SX porous membrane samples made of nitrocellulose were laminated onto corresponding supporting cards having a length of approximately 30 centimeters. C-reactive protein (CRP) monoclonal antibody (Mab A58040136P, 2.3 mg/ml, obtained from BiosPacific, Inc. of Emeryville, Calif.) was striped onto the membrane to form a detection line. Goldline (a polylysine solution obtained from British Biocell International) was then striped onto the membrane to form a calibration line. The membrane was dried for 1 hour at 37° C.

A cellulosic fiber wicking pad (Millipore Co.) was attached to one end of the membrane. The other end of the membrane was laminated with two glass fiber pads (sample and conjugate pads) obtained from Millipore Co. The conjugate pad and wicking pad were in direct contact with the membrane, and the sample pad was in direct contact with the conjugate pad. The conjugate pad and sample pad each had a width of 4 millimeters. The sample pad was treated with 1% polyoxyethylene sorbitan monolaurate (a nonionic surfactant available from Sigma-Aldrich under the name "Tween 20") and dried at 37° C. for 2 hours. The conjugate pad was treated with 200 microliters of the conjugated probe particles of Example 1, mixed with a PBS buffer, 200 microliters of 2% "Tween 20", and 200 microliters of 20% sucrose. The soaked conjugate pad was dried in an oven for 1.5 hours at 37° C.

The resulting devices were sealed in a bag for storage.

EXAMPLE 4

The ability of the device of Example 3 to detect the presence of an analyte was determined. Specifically, eight full samples of the devices of Example 3 were provided. 40 microliters of CRP solution of different concentrations in PBS (i.e., 0, 1, 2, 5, 10, 20, 50 and 100 nanograms per milliliter) was directly applied to the sample pads of each sample, respectively. The devices were allowed to develop for 30 minutes and fluorescence on both detection line and calibration line was measured at excitation wavelengths of 370 nanometers and 611.5 nanometers, respectively. Fluorescence was measured with a conventional FluoroLog III spectrofluorometer (purchased from Horiba Group) using a front face mode. The excitation beam was aligned about 70° relative to the device surface normal and about 45° relative to the device surface normal for the emission. Although the reactions were visually observed to be complete within about 15 minutes, enough time was allowed for full reaction before taking the fluorescence measurements.

Table I gives the fluorescence data for both calibration and detection lines.

TABLE I

| | Fluorescence Data | | | | | | | |
|---|---|---|---|---|---|---|---|---|
| Sample No. | 1 | 2 | 3 | 4 | 5 | 6 | 7 | 8 |
| CRP Added (ng/ml) | 0 | 1 | 2 | 5 | 10 | 20 | 50 | 100 |
| Detection Line Intensity, $I_s$ (x10-3) | 19.7 | 27.2 | 34.7 | 75.8 | 89.1 | 170 | 336 | 402 |
| Calibration Line Intensity, $I_c$ (x10-3) | 773 | 825 | 818 | 672 | 540 | 500 | 563 | 289 |

Figure 6:
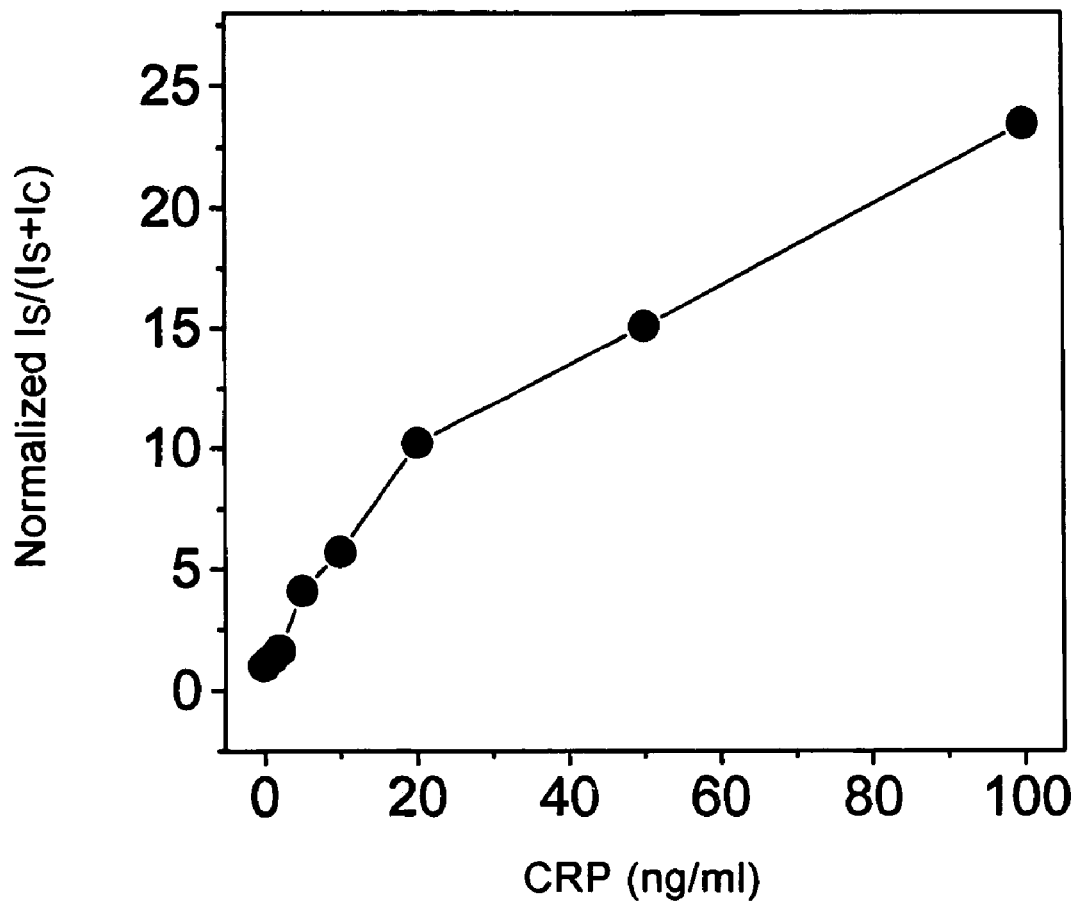
FIG. 6 is a graph of normalized fluorescent intensity versus analyte concentration (nanograms per milliliter) for the results obtained in Example 4.

The normalized intensity ratio of $I_s/(I_s+I_c)$ versus CRP concentration is shown in FIG. 6. Normalized intensity was obtained by dividing the measured fluorescence intensity of the sample by the fluorescence intensity of a control sample. As shown, the dose response curve is calibrated by the calibration line and is linear, particularly for CRP concentrations less than 20 nanograms per milliliter.

EXAMPLE 5

The ability of the device of Example 3 to detect the presence of an analyte was determined. Specifically, five groups that each contained four full samples of the devices of Example 3 were provided. 40 microliters of CRP solution of different concentrations in PBS (i.e., 0, 1, 2, and 5 nanograms per milliliter) was directly applied to the sample pads. The devices were allowed to develop for 30 minutes and fluorescence on both detection line and calibration line was measured at excitation wavelengths of 370 nanometers and 611.5 nanometers, respectively. Fluorescence was measured with a conventional FluoroLog III spectrofluorometer using a front face mode. The excitation beam was aligned about 70° relative to the device surface normal and about 45° relative to the device surface normal for the emission. Although the reactions were visually observed to be complete within about 15 minutes, enough time was allowed for full reaction before taking the fluorescence measurements.

Tables II and III give the data for both the calibration and detection lines.

TABLE II

Fluorescence Data ($I_s/I_c$)

| | \multicolumn{5}{c}{Group} |
|---|---|---|---|---|---|
| | 1 | 2 | 3 | 4 | 5 |
| CRP Added (ng/ml) | | | | | |
| 0 | 413/1.7 | 453/1.6 | 416/1.5 | 558/1.9 | 455/1.9 |
| 1 | 460/1.7 | 472/1.9 | 525/1.7 | 474/1.4 | 631/1.6 |
| 2 | 627/2.0 | 575/1.2 | 572/1.7 | 601/1.4 | 534/2.0 |
| 5 | 708/1.3 | 778/1.3 | 638/1.3 | 743/1.6 | 816/1.6 |

TABLE III

Average Fluorescence Intensity / Standard Deviation ($I_s/I_s + I_c$)

| Group | ($I_s/I_s + I_c$) | $I_s$ |
|---|---|---|
| CRP Added (ng/ml) | | |
| 0 | 0.2110/0.0150 | 458/59 |
| 1 | 0.2367/0.0331 | 512/71 |
| 2 | 0.2573/0.0418 | 582/35 |
| 5 | 0.3422/0.0222 | 738/68 |

Thus, as a result of the present invention, background interference from many sources, such as scattered light and autofluorescence, can be practically eliminated during detection. In addition, the fluorescent reader used in the present invention can have a simple and inexpensive design. For instance, in one embodiment, the reader can utilize a pulsed light-emitting diode (LED) and a silicon photodiode to accurately excite labels and detect fluorescence on a membrane-based assay device without requiring the use of expensive components, such as monochromators or narrow emission band width optical filters.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting the presence or quantity of an analyte residing in a test sample, said method comprising:
   i) providing a flow-through assay device that comprises a porous membrane in fluid communication with a conjugate pad, the conjugate pad including probes comprising particles modified with a specific binding member configured to bind with the analyte and containing a fluorescent label, said fluorescent label having a fluorescence emission lifetime of greater than about 1 microsecond, said porous membrane defining a detection zone within which is immobilized a capture reagent configured to bind with the analyte, and wherein the porous membrane defines a calibration zone positioned downstream from the detection zone within which is immobilized a capture reagent configured to bind with the probes;
   ii) contacting the conjugate pad with the test sample and allowing the particles to flow to said detection zone and said calibration zone;
   iii) subjecting the detection zone to pulses of illumination to generate a detection signal and, after a certain period of time has elapsed following a pulse, measuring the intensity of the detection signal, wherein a fluorescence reader is employed to provide the illumination and measure the intensity of the detection signal, the reader comprising a pulsed excitation source and a time-gated detector;
   iv) subjecting the calibration zone to pulses of illumination to generate a calibration signal and after a certain period of time has elapsed following a pulse, measuring the intensity of the calibration signal; and
   v) comparing the intensity of the detection signal to the intensity of the calibration signal, wherein the amount of the analyte within the test sample is proportional to the intensity of the detection signal as calibrated by the calibration signal.

2. The method of claim 1, wherein said fluorescent label has an emission lifetime of greater than about 10 microseconds.

3. The method of claim 1, wherein said fluorescent label has an emission lifetime of from about 100 to about 1000 microseconds.

4. The method of claim 1, wherein said fluorescent label has a Stokes shift greater than about 50 nanometers.

5. The method of claim 1, wherein said fluorescent label has a Stokes shift of greater than about 100 nanometers.

6. The method of claim 1, wherein said fluorescent label has a Stokes shift of from about 250 to about 350 nanometers.

7. The method of claim 1, wherein said fluorescent label includes a lanthanide chelate of samarium, dysprosium, europium, terbium, or combinations thereof.

8. The method of claim 1, wherein said fluorescent label is europium chelate.

9. The method of claim 1, wherein said detection zone includes multiple detection regions.

10. The method of claim 9, wherein said detection regions contain multiple capture reagents for binding to multiple analytes.

11. The method of claim 1, wherein the detection zone and the calibration zone are simultaneously subjected to pulses of illumination.

12. The method of claim 1, wherein the intensity of said detection signal and the intensity of said calibration signal are measured simultaneously.

13. The method of claim 1, wherein said pulsed excitation source is a light-emitting diode.

14. The method of claim 1, wherein said time-gated detector is a silicon photodiode.

15. The method of claim 1, wherein an optical filter is positioned adjacent to said pulsed excitation source, said time-gated detector, or combinations thereof.

16. The method of claim 1, wherein the fluorescence reader is employed to provide the illumination and measure the intensity of the detection signal and the intensity of the calibration signal, the reader comprising timing circuitry in communication with the pulsed excitation source and the time-gated detector.

17. The method of claim 1, wherein the intensity of the detection signal is measured after about 100 to about 200 microseconds.

18. The method of claim 1, wherein the capture reagent of the detection zone is an antigen or antibody.

19. The method of claim 18, wherein the specific binding member is an antigen or antibody.

20. The method of claim 1, wherein the capture reagent of the calibration zone is a polyelectrolyte.

21. The method of claim 20, wherein the polyelectrolyte is configured to bind to the particles.

22. The method of claim 1, wherein the amount of particles exceeds the amount of available binding sites in the detection zone.

23. The method of claim 1, wherein the capture reagents of the detection zone and the calibration zone are substantially non-diffusively immobilized on the porous membrane.

24. The method of claim 1, wherein the particles are diffusively immobilized on the conjugate pad.

25. The method of claim 1, wherein the particles are latex particles.

26. The method of claim 10, wherein each said detection region contains different capture reagents.

27. The method of claim 1, wherein the intensity of the detection signal is measured after a certain period of time has elapsed following each pulse.

28. The method of claim 1, wherein the intensity of the calibration signal is measured after a certain period of time has elapsed following each pulse.

* * * * *

UNITED STATES PATENT AND TRADEMARK OFFICE
CERTIFICATE OF CORRECTION

PATENT NO. : 7,632,653 B2 Page 1 of 1
APPLICATION NO. : 10/286342
DATED : December 15, 2009
INVENTOR(S) : Song et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 980 days.

Signed and Sealed this

Second Day of November, 2010

David J. Kappos
*Director of the United States Patent and Trademark Office*